US010857306B2

(12) United States Patent
Holmqvist et al.

(10) Patent No.: US 10,857,306 B2
(45) Date of Patent: Dec. 8, 2020

(54) SYRINGE

(71) Applicant: GALDERMA S.A., Cham (CH)

(72) Inventors: Anders Holmqvist, Värmdö (SE); Max Blomqvist, Uppsala (SE); Jonas Törnsten, Uppsala (SE)

(73) Assignee: GALDERMA S.A., Cham (CH)

( * ) Notice: Subject to any disclaimer, the term of this patent is extended or adjusted under 35 U.S.C. 154(b) by 231 days.

(21) Appl. No.: 16/066,940

(22) PCT Filed: Dec. 21, 2016

(86) PCT No.: PCT/EP2016/082074
§ 371 (c)(1),
(2) Date: Jun. 28, 2018

(87) PCT Pub. No.: WO2017/114708
PCT Pub. Date: Jul. 6, 2017

(65) Prior Publication Data
US 2019/0015597 A1 Jan. 17, 2019

(30) Foreign Application Priority Data

Dec. 29, 2015 (EP) ..................................... 15202926

(51) Int. Cl.
*A61M 5/315* (2006.01)
*A61M 5/178* (2006.01)
*A61M 5/31* (2006.01)

(52) U.S. Cl.
CPC ........ *A61M 5/31578* (2013.01); *A61M 5/178* (2013.01); *A61M 5/3148* (2013.01);
(Continued)

(58) Field of Classification Search
CPC ............ A61M 5/31541; A61M 5/3157; A61M 5/3158; A61M 5/31578; A61M 5/178;
(Continued)

(56) References Cited

U.S. PATENT DOCUMENTS

| 5,279,585 A | 1/1994 | Balkwill |
| 5,725,508 A | 3/1998 | Chanoch et al. |
| (Continued) | | |

FOREIGN PATENT DOCUMENTS

| EP | 0 554 995 A1 | 8/1993 |
| EP | 0 688 571 A1 | 12/1995 |
| (Continued) | | |

OTHER PUBLICATIONS

International Preliminary Report on Patentability (Form PCT/IPEA/409) dated May 3, 2018, by the Patent corporation Treaty in Corresponding International Application No. PCT/EP2016/082074 (15 pages).

(Continued)

*Primary Examiner* — Manuel A Mendez
(74) *Attorney, Agent, or Firm* — Foley & Lardner LLP; Sunit Talapatra (57) ABSTRACT

A syringe including a barrel, a plunger moveably arranged within said barrel and a plunger rod for driving said plunger is provided. The syringe includes a first engagement member arranged at the plunger rod such that a longitudinal movement of the plunger rod yields a rotational movement of said first engagement member, said first engagement member including a grooved surface, and a second engagement member arranged at the barrel to engage with said grooved surface of the first engagement member such that feedback is given to a user as the plunger rod is moved relative to the barrel for driving said plunger. Wherein, for a given distance D travelled by the plunger rod relative to the barrel, a point of the grooved surface of the first engagement member moves a distance d, wherein d≥D.

14 Claims, 2 Drawing Sheets

(52) U.S. Cl.
CPC .... *A61M 5/31568* (2013.01); *A61M 5/31575* (2013.01); *A61M 5/3158* (2013.01); *A61M 2205/581* (2013.01); *A61M 2205/582* (2013.01)

(58) Field of Classification Search
CPC .......... A61M 5/31575; A61M 5/31568; A61M 5/31573; A61M 5/31566; A61M 5/31565; A61M 5/31511; A61M 5/315; A61M 5/2033; A61M 5/31551; A61M 5/20; A61M 5/31526; A61M 5/31501; A61M 2205/581; A61M 2205/582
See application file for complete search history.

(56) References Cited

U.S. PATENT DOCUMENTS

| | | | |
|---|---|---|---|
| 9,345,839 | B2* | 5/2016 | Shetty ............... A61M 5/31526 |
| 2010/0094206 | A1 | 4/2010 | Boyd et al. |
| 2012/0265151 | A1 | 10/2012 | Nzike et al. |
| 2012/0289908 | A1 | 11/2012 | Kouyoumjian et al. |
| 2013/0197449 | A1 | 8/2013 | Franklin |
| 2015/0238699 | A1 | 8/2015 | Butler et al. |
| 2015/0250950 | A1 | 9/2015 | Moser et al. |
| 2016/0038682 | A1 | 2/2016 | Toprnsetn et al. |
| 2016/0271332 | A1* | 9/2016 | Bilton ..................... A61M 5/20 |

FOREIGN PATENT DOCUMENTS

| | | |
|---|---|---|
| EP | 1 923 083 A1 | 5/2008 |
| EP | 2 783 720 A1 | 10/2014 |
| WO | 2006/079481 A1 | 8/2006 |
| WO | WO 2008/057976 A2 | 5/2008 |
| WO | WO 2011/039236 A1 | 4/2011 |
| WO | WO 2014/040929 A1 | 3/2014 |
| WO | WO 2014/056635 A1 | 4/2014 |
| WO | 2014/153572 A1 | 9/2014 |
| WO | WO 2015/032778 A1 | 3/2015 |

OTHER PUBLICATIONS

International Search Report (PCT/ISA/210) dated Apr. 26, 2017, by the European Patent Office as the International Searching Authority for International Application No. PCT/EP2016/082074.

Written Opinion (PCT/ISA/237) dated Apr. 26, 2017, by the European Patent Office as the International Searching Authority for International Application No. PCT/EP2016/082074.

International Preliminary Report on Patentability (PCT/IPEA/409) dated Apr. 16, 2018, by the European Patent Office as the International Searching Authority for International Application No. PCT/EP2016/082074.

International Search Report (PCT/ISA/210) dated Apr. 12, 2017, by the European Patent Office as the International Searching Authority for International Application No. PCT/EP2016/082077.

Written Opinion (PCT/ISA/237) dated Apr. 12, 2017, by the European Patent Office as the International Searching Authority for International Application No. PCT/EP2016/082077.

International Preliminary Report on Patentability (PCT/IPEA/409) dated Apr. 16, 2018, by the European Patent Office as the International Searching Authority for International Application No. PCT/EP2016/082077.

* cited by examiner

SYRINGE

TECHNICAL FIELD

The present invention generally relates to syringes, and more particularly to a syringe that is able to provide a user with feedback during use.

TECHNICAL BACKGROUND

When a user of a medical syringe administers a substance, it is common, in particular within certain areas of treatment, to distribute the total volume carried by the syringe over an area. Some examples of such areas of treatment are dermatology, plastic surgery, cosmetic surgery, and odontology. The distribution is for instance done by inserting the needle of the syringe just beneath and approximately in parallel with the skin surface and then administering the substance while withdrawing the needle. Another way is to administer the substance at several anatomic locations within a limited area, i.e. to administer a fraction of the total volume at each location.

In these, and other, methods of distributing the substance it is an advantage if the syringe is provided with some kind of dosing aid, which aids the user in knowing how large a fraction of the total volume of the substance is administered at each location or per time unit.

One known example of dosing aids is the dosing scale traditionally provided on syringes, where known problems include difficulties for a user to see the scale during injection as well as the distraction of attention arising when the user simultaneously tries to read the scale and perform the injection.

Also known are mechanical and electronic injectors. These devices however tend to be more expensive and heavier than traditional syringes. Further problems include the fact that most injectors do not allow aspiration prior to injection, which possesses a considerable drawback for many users.

In order to alleviate some of these drawbacks, attempts have been made to provide a syringe with user friendly means that informs and provides feedback to a user about the injected amount or an injection rate. For example, an effort to provide a syringe with a dosing aid is disclosed in WO2008057976 where an engagement member is provided on the finger grip and engages with a structure of the plunger rod.

However, tests have proven that a first dose with such prior art constructions can be up to three time larger than actually intended and such overdosing can in certain situations be catastrophic for patients causing e.g. unintended muscle paralysis which in turn may cause problems with respect to swallowing, speaking, or breathing, drooping eyelids, lopsided smile, muscle weakness and/or muscle stiffness.

Further, problems related to the syringe not providing distinct feedback during certain conditions, such as when the plunger rod is moved at a slow speed with respect to the barrel are also known from the prior art.

SUMMARY OF THE INVENTION

Accordingly, it would be desirable to provide an improved syringe providing feedback to a user during injection about for example the amount delivered. In particular, it would be desirable to provide a more distinct feedback while at the same time increasing the accuracy of the delivered dosage.

To better address one or more of these concerns a syringe as defined in the independent claim is provided. Preferred embodiments are defined in the dependent claims.

According to a first aspect of the invention a syringe comprising a barrel, a plunger moveably arranged within said barrel and a plunger rod for driving said plunger is provided. The syringe comprises a first engagement member arranged at the plunger rod, such that a longitudinal movement of the plunger rod yields a rotational movement of said first engagement member, said first engagement member comprising a grooved surface and a second engagement member arranged at the barrel to engage with said grooved surface of the first engagement member such that feedback is given to a user as the plunger rod is moved relative to the barrel for driving said plunger. For a given distance D travelled by the plunger rod relative to the barrel, a point of the grooved surface of the first engagement member moves a distance d, wherein d≥D.

According to the first aspect, the syringe provides an inventive solution to the concerns described above derived from the realization that the desired functionality may be provided by a design incorporating a first and second engagement member, the first engagement member being arranged at the plunger rod, further arranged such that a feedback is provided to the user as the plunger rod is moved relative the barrel, wherein for a given distance D travelled by the plunger rod relative the barrel, the first engagement member moves a distance d, wherein the distance d moved, or travelled, by the first engagement member is equal to or larger than the distance D travelled by the plunger rod.

Hereby, i.e. by designing the device such that the distance travelled by the first engagement member, although arranged at the plunger rod, may be different than the corresponding distance travelled by the plunger rod, the size of a dose to be delivered no longer imposes the same constraints on the design of the functionality providing a feedback to a user. Therefore, the improved syringe may provide a distinct feedback while at the same time the accuracy of the delivered dose of a substance may be increased, for example with regards to a first dose and the feedback delivered after a reversal of the direction of movement of the plunger rod. Accordingly, advantages of the invention include that the dosage accuracy may be significantly improved while, at the same time, the feedback to the user may be made more distinct.

The disclosed syringe is suitable for example for applications wherein the syringe is supplied empty. During use, the substance to be injected is first drawn up in to the barrel of the syringe for example from a vial. Examples of such substances include botulinum toxin. In certain application, the substance is then administered to the patient in multiple steps and/or at different injection locations. Due to the design of the syringe, and more particularly the design of the first and second engagement members, a feedback is repeated when the substance is injected, each feedback indication normally corresponds to a certain dose of the substance. The syringe may in some embodiments be a disposable syringe. Suitable materials for the comprised components include plastics, further suitable manufacturing methods include injection moulding. The barrel of the syringe is adapted to contain the substance to be administered. The plunger is movably arranged within said barrel and a plunger rod is provided to drive said plunger, in order to for example expel the substance contained in the barrel to be administered through a cannula attached to the barrel or in some cases draw the substance into the syringe.

The first engagement member is arranged on the plunger rod and comprises a grooved surface, i.e. a surface comprising grooves and/or ridges/ribs. The number of grooves, or ridges as well as the distance between the adjacent grooves may be adapted depending on the application. In some embodiments, the first engagement member moves, or travels, in a direction coinciding with a direction of movement of the plunger rod. In some embodiments, the first engagement member moves, or travels, in a direction different from a direction of movement of the plunger rod. By the term moves, or travels, any movement performed by the first engagement member may be understood such as a translational movement or in some embodiments a rotational movement. The distance d may in some embodiments refer to a magnitude of a movement or to a distance travelled along a specified direction or along a specified path.

The second engagement member is adapted to engage with the grooved surface of the first engagement member in order to provide feedback to the user as the plunger rod, on which the first engagement member is arranged, is moved with respect to the barrel. Accordingly, the second engagement member may in some embodiments be arranged at, or connected to, the barrel. Other examples include embodiments wherein the second engagement member is arranged at other parts stationary with respect to the barrel, such as for example a finger grip. Commonly, the second engagement member is stationary arranged with respect to the plunger rod in order to provide feedback as the plunger rod moves with respect to the barrel. According to one embodiment, the second engagement member is arranged adjacent to an end of the barrel, according to one embodiment, the second engagement member is arranged within the barrel.

One possible form of feedback that may in some embodiments be provided by the second engagement member, and/or by the second engagement member interacting or engaging with the first engagement member is an audible feedback, i.e. a sound such as a click-sound. Other examples include tactile feedback. In some embodiments, each feedback indication may correspond to the second engagement member travelling over one groove (or ridge) of the first engagement member.

In order to achieve a reliable, distinct feedback indication regardless of for example the travelling speed of the plunger rod, the invention according to the independent claims comprise a design wherein the first engagement member is arranged at the plunger rod such that for a given distance D travelled by the plunger rod relative the barrel, the first engagement member moves a distance d, wherein the distance d moved, or travelled, by the first engagement member is equal to or larger than the distance D travelled by the plunger rod. For example, in one embodiment, for a given distance D travelled by the plunger rod relative the barrel, a point of the grooved surface of the first engagement member moves (travels) a distance d, wherein d≥D.

Accordingly, in some embodiments, the distance travelled by the plunge rod, for example a distance travelled by the plunger in order to deliver a dose, may be different than the distance travelled by the first engagement member, for example smaller. This may be particularly advantageous for examples in applications wherein the dose to be delivered, and consequently, the distance travelled by the plunger for each dose, is very small. In such a case, the distance moves by the first engagement member may be made larger than the distance travelled by the plunger rod.

The implications of this functionality of the independent claims may be better understood when described in combination with the functionality of the engagement between the first and the second engagement member. The second engagement member is arranged to engage the grooved surface of the first engagement member in order to provide feedback as the plunger rod moves. This engagement may in an exemplary embodiment take place over a certain distance. Due to the larger distance travelled by the first engagement member, the engagement between the first and second engagement member, i.e. the engagement of the second engagement member with the grooved surface, may be allowed over a larger distance, e.g. the distance travelled by the first engagement member corresponding to one dose. Such a distance over which the engagement is allowed may be referred to as an interaction distance. Small travelling distances, e.g. small distances of interaction, may be associated with problems relating to dosage accuracy and distinctiveness of the provided feedback. For example, in an exemplary case wherein the interaction distance would be very small, a second engagement member may have to be designed comprising an impractically high stiffness.

With regards to the claimed invention, for example an engagement wherein the second member is allowed to move in and out of engagement with the first engagement member (or vice versa) during the injection may be provided. The first engagement member is arranged on the plunger rod and moves as the plunger rod moves relative the barrel. The first engagement member further comprises grooves with which the second engagement member engages as the plunger rod moves with respect to the barrel. Ribs or protrusions are arranged between adjacent grooves.

In the exemplary embodiment, the second engagement member may move in and out of engagement with the first engagement member as the plunger rod and the first engagement member moves. For example, in a first stage of engagement, the second engagement member may move together with the first engagement member, i.e. be guided by the first engagement member, and in a second stage, the second engagement member may move independently, i.e. freely, from the first engagement member. For example, in one embodiment, the second engagement member may in the first stage slide along a first rib arranged between adjacent grooves. At a top of the rib, the second engagement member may move out of engagement with the first engagement member. During this second stage, the second engagement member may move independently of the first engagement member and may accelerate back to an initial position. During the described course of engagements, a dose may be delivered by the syringe. A feedback indication may be provided as the second engagement member moves back into engagement with the first engagement member, for example as the movement of the second engagement member is stopped by the first engagement member, for example by a following groove (or rib) of the grooved surface. In other, a free acceleration of the second engagement member is allowed for example as the second engagement member moves out of engagement with the first engagement member.

Accordingly, the engagement between the first and the second engagement member may in some embodiment be described as an engagement at least partly adapted to stop a movement of the second engagement member, for example a free movement, in order to provide a distinct feedback which in some embodiments may be an audible sound and/or tactile feedback. Due to for example the allowed freedom in choosing the distance to be travelled by the first engagement member with respect to the distance travelled by the plunger rod, and hence the distance of interaction of the first and second engagement members, a reliable mechanism for producing a feedback may be ensured irrespective of the substances and dose sizes to be delivered. This stands in contrast to the problems of the known art related to for example lack of sufficient acceleration of comprised parts, such as for example when a plunger rod of the prior art is moved slowly and one engagement member slowly slides along another thereby not producing a distinct feedback.

Further, due to the design, wherein for example a larger distance of interaction, or engagement may be allowed, less constrain may be put on the design of the grooved surface. For example, a larger distance (as compared to the corresponding distance travelled by the plunger rod) between adjacent grooves, or ribs, may be provided. Apart from the advantageous effect of a larger interaction distance described in the foregoing, larger ribs may also provide the advantageous effect of a decrease of the demands on component tolerances.

A further advantage of the disclosed syringe is that due to the design of the present first engagement member, known problems relating to the accuracy of dosage and the feedback provided, in particularly the accuracy of the first dose administered after the substance has been drawn into the syringe from a vial or the like, are reduced. For example, the size of the dose delivered following a change of direction of the plunger rod such as the first dose delivered after a substance has been drawn into the syringe. As the direction is reversed, known problems relating to a too large movement of the plunger rod before feedback is again provided to the practitioner must be avoided. Such large movements, and consequently a delivery of a to large dose, may be associated with problems such as causing e.g. unintended muscle paralysis which in turn may cause problems with respect to swallowing, speaking, or breathing, drooping eyelids, lopsided smile, muscle weakness and/or muscle stiffness. According to the invention, due to the different distances of movement allowed between the plunger rod and the first engagement member however, a small plunger rod movement and consequently a sufficiently low dose of the substance, may be combined with a larger movement of the first engagement member and consequently a sufficiently large interaction distance provided for the engagement between the first and second engagement member, should this prove necessary for providing a proper and distinct feedback.

Further, due to for example the acceleration of the second engagement member allowed in some embodiments, not only is a distinct feedback provided to a user but a situation such as what is known from the prior art wherein the first engagement member may stop to an undesired rest at an intermediate position between ridges when the plunger rod moves slowly, thereby allowing a to large dose to be administered when travelling along to provide a next feedback to the user is highly unlikely to occur in the present invention.

According to one embodiment, d>D. I.e., the distance d travelled by the first engagement member may be larger than the distance D travelled by the plunger rod. This may be particularly advantageous when providing substances in very small doses, i.e. substances associated with very small plunger rod movements. A larger movement of the first engagement member, and consequently a larger distance of interaction for the first and the second engagement members may allow for a preferred feedback regardless of for example dose size.

According to one embodiment, for a given distance D travelled by the plunger rod relative the barrel, the first engagement member, and more particularly a point of its grooved surface. is adapted to move, or travel, a distance d, irrespective of the direction of movement of the plunger rod. This may in some embodiments imply that the feedback to the user is generated irrespective of the travelling direction of the plunger rod. Accordingly, feedback may be provided not only during injection, but also when filling the syringe, i.e. when drawing fluid into the syringe. This is of particular importance for example for the first dose after filling the syringe, i.e. the first feedback indication. Prior to the delivery of the first dose, the direction of movement of the plunger rod is reversed. Due to the design of the arrangement of the first engagement member and the plunger rod and the functionality of the engagement of the first and second engagement members as described in the preceding paragraphs, the design easily lends itself to what may in some embodiments be described as a symmetric layout wherein the behaviour of the comprised components is substantially the same regardless of the direction of movement of the plunger rod.

According to one embodiment, the first engagement member and the second engagement member move substantially in a common plane A. The plane may for example be a plane through the first engagement member.

According to one embodiment, said plane A is a plane normal to the direction of movement of said plunger rod. In other words, a plane generally perpendicular to a longitudinal direction of said plunger rod as the plunger rod is moved relative to the barrel. Examples include a second engaging member may be an engaging member comprising a flexible member, such as a spring, arm or tongue, or the like adapted to move in said plane. According to one embodiment, the engaging member moves in a radial direction of the barrel.

According to one embodiment, the plunger rod and the first engagement member are arranged such that a gear mechanism is provided by means of the engagement between said plunger rod and said first engagement member. Such a gear mechanism is one way of achieving the difference in corresponding distances of movement between the plunger rod and the first engagement member, i.e. By gear mechanism, a mechanism adapted to change the ratio between the distances D and d, defined in the foregoing is to be understood. In one exemplary embodiment, such a gear mechanism, or gear box mechanism, may be provided by means of a threaded engagement.

According to one embodiment, a longitudinal movement of the plunger rod yields a rotational movement of the first engagement member. Accordingly, when the plunger rod travels with respect to the barrel, the first engagement member rotates and the second engagement member may engage the rotating grooves (and ridges). A design wherein a rotational movement of the engagement member is induced is an advantageously space efficient design. The first engagement member may be arranged to rotate substantially in the plane a mentioned above. In one embodiment, the grooves of the grooved surfaces are adapted to extend in a direction parallel to the longitudinal axis of the plunger rod. In one embodiment, the grooves of the grooved surface of the first engagement member are adapted to extend in a direction such that a tangent to one of the grooves is perpendicular to the longitudinal axis of the plunger rod.

According to one embodiment, the syringe further comprises a guiding element adapted to restrain a rotational movement of said plunger rod. Hereby, the rotation of the plunger rod may be constrained and the first engagement member may be rotated as the plunger rod is moved longitudinally, i.e. in and out of the barrel.

According to one embodiment, the guiding element comprises a hole adapted to receive the plunger rod, the hole comprising means for constraining a rotation of said plunger rod. In one embodiment, said means comprise a first and second flat surface of the hole through which the plunger may be received. In one embodiment, the plunger rod comprises a first and a second substantially flat surface adapted to engage said first and second corresponding flat surface of the hole, such that a rotation is constrained.

According to one embodiment, a guiding element adapted to restrain a rotational movement of said plunger rod may be arranged at a finger grip of the syringe. Hereby, the rotation of the plunger rod may be constrained and the click wheel may be rotated as the plunger rod is moved longitudinally, i.e. in and out of the barrel. According to one embodiment, the guiding element adapted to restrain a rotational movement of said plunger rod is formed at the finger grip and/or as an integral component with said finger grip.

According to one embodiment, the plunger rod comprises at least one of a helical groove and a helical protrusion. The pitch of the helical groove may be chosen to fit different applications. A lower pitch may be preferable in order to lower the resisting force when the plunger rod is pushed by the user. In one embodiment, the at least one helical groove or protrusion may be referred to as a thread, or threading, of the plunger rod. In one embodiment, the pitch may be adapted to the number of grooves and/or the distance between adjacent grooves of the grooved surface of the second engagement member. Further, the pitch may be also be chosen based on other important, interacting, parameters of the syringe such as size of the first engagement member, the number and shape of the grooves and ridges of the grooved surface as well as the design of the second engagement member.

According to one embodiment, the first engagement member comprises means for engaging said at least one of a helical groove and a helical protrusion. In one embodiment, said means comprise a corresponding helical groove or protrusion to that of plunger rod. In some embodiments, such a helical groove or protrusion may be referred to as a thread, or threading, of the plunger rod. Accordingly, the first engagement member may be arranged on the plunger rod by means of a thread fitting.

According to one embodiment, at least a portion of said second engagement member is movable between a first stage, wherein said at least one portion of said second engagement member engages with a groove and a second stage wherein said at least one portion of said second engagement member engages a protrusion. Such a protrusion is a protrusion between adjacent grooves, i.e. a protruding structure separating two grooves which may also be referred to as a rib. According to one embodiment, the at least one portion comprises an elastic element adapted to engage the grooved surface of the first engagement member. Examples include a spring element made of plastic, a spring element made of metal such as for example feather steel, a sheet metal element, a steel wire element or a metal or plastic tongue. Such an elastic element may be movably arranged.

According to one embodiment, the at least one portion of said second engagement member is movable between said first stage and said second stage by means of a deflection. Accordingly, for a given distance D travelled by the plunger rod relative the barrel, at least a portion of the second engagement member is adapted to deflect a distance d, wherein d≥D. Further, according to one embodiment, for a given distance D travelled by the plunger rod relative the barrel, at least said option of said second engagement member is adapted to deflect a distance d, irrespective of the direction of movement of the plunger rod.

According to one embodiment, at least a portion of the second engagement member is tensioned at least in said second stage. In one embodiment, the engaging member is a tensioned, or biased, elastic element. Examples include a spring element made of plastic, a spring element made of metal such as for example feather steel, a sheet metal element, a steel wire element or a metal or plastic tongue. The tensioning of the engaging member further contributes to the improvement of the feedback produced, i.e. the click-sound, at least in part since a tensioned engagement member may be designed to snap back to its initial position (i.e. the first stage) when a desired dose size is achieved.

According to one embodiment, at least one portion of the second engagement member is untensioned, i.e. relaxed in said first stage. In such an embodiment, in contrast to the disclosed second stage, the at least one portion is not biased, or tensioned, in said first stage.

According to one embodiment, the second engagement member comprises an engaging member adapted to engage the grooved surface of the first engagement member. Such an engaging member may in some embodiments comprise a protruding element further adapted to engage said grooved surface. Such a protruding element may improve the engagement between the first and second engagement element. Examples include a hatch, a ratchet or a hook. In one embodiment, the protruding element is arranged to protrude from an elastic member of the engaging element.

According to one embodiment, the second engaging element comprises at least a first and a second portion adapted to engage the grooved surface of the first engagement member, wherein the at least two portions are movable between a first stage, wherein the first and second portion respectively engage with a groove and a second stage wherein the first and second portion respectively engage a protrusion.

According to one embodiment, the second engagement member comprises an elongated flexible structure adapted to be fixed at the barrel at a first end and to engage the grooved surface at a second end. The elongated structure may comprise a plurality of bent portions. The elongated structure may further be referred to as a click-spring.

According to one embodiment, the first engagement member is a wheel, or comprises a wheel shape. Such a first engagement member is space efficient and especially suitable for a case wherein the relative rotational movement between the first engagement member and the plunger rod is at least partly rotational. The wheel may comprise the surface comprising grooves, or ridges and may further be referred to as a click-wheel.

According to one embodiment, the number of grooves of the grooved surface of the first engagement element lies in the range of 1-15, preferably in the range of 5-10.

Further, according to one embodiment, the distance travelled by the plunger rod corresponding to the second engagement moving between two adjacent grooves (or ridges) of the first engagement element, lies in the interval of 0-5 mm, preferably in the interval of 0.5-2 mm. According to one embodiment, the volume of (the barrel) of the syringe lies in the interval of 0-5 ml, preferably in the interval of 0.25-0.75 ml. According to one embodiment, the inner diameter of (the barrel) of the syringe lies in the interval of 0-5 mm, preferably in the interval of 2-4 mm.

Further objectives of, features of and advantages with the present invention will become apparent when studying the following detailed disclosure, the drawings and the appended claims. Those skilled in the art realize that different features of the present invention can be combined to create embodiments other than those described in the following.

BRIEF DESCRIPTION OF THE DRAWINGS

The invention will be better understood through the following illustrative and non-limiting detailed description of preferred embodiments, with reference to the appended drawing, on which.

All figures are schematic, not necessarily to scale, and generally only show parts which are necessary in order to elucidate the invention, wherein other parts may be omitted or merely suggested.

DETAILED DESCRIPTION OF EMBODIMENTS

Figure 1:
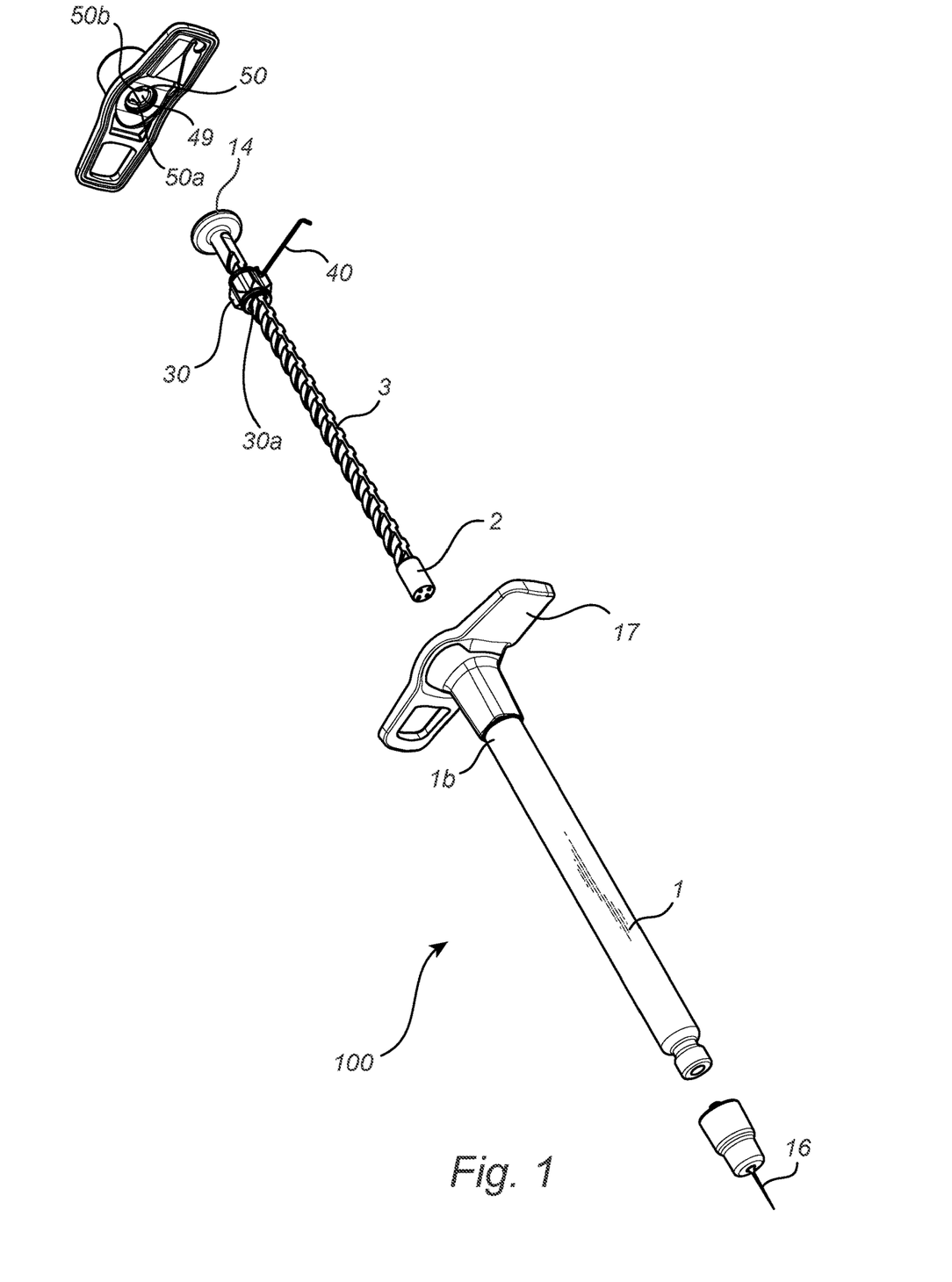
FIG. 1 is an exploded view of a syringe according to one embodiment of the invention.

A syringe 100 according to an embodiment of the invention is shown in an exploded view in FIG. 1. The syringe comprises a barrel 1, a plunger 2 moveably arranged within the barrel 1 and a plunger rod 3 for driving the plunger 2. The plunger rod is further provided with a thumb plate 14 for activation of the plunger rod 3. The plunger rod 3 is adapted to drive the plunger 2, i.e. to engage the plunger 2 such that the plunger 2 may preferably be moved in both directions through the barrel. Suitable engagement means may be provided to allow for this engagement. The syringe 100 further comprises a needle 16. The syringe is further provide with a finger grip 17 arranged at the barrel.

Figure 2:
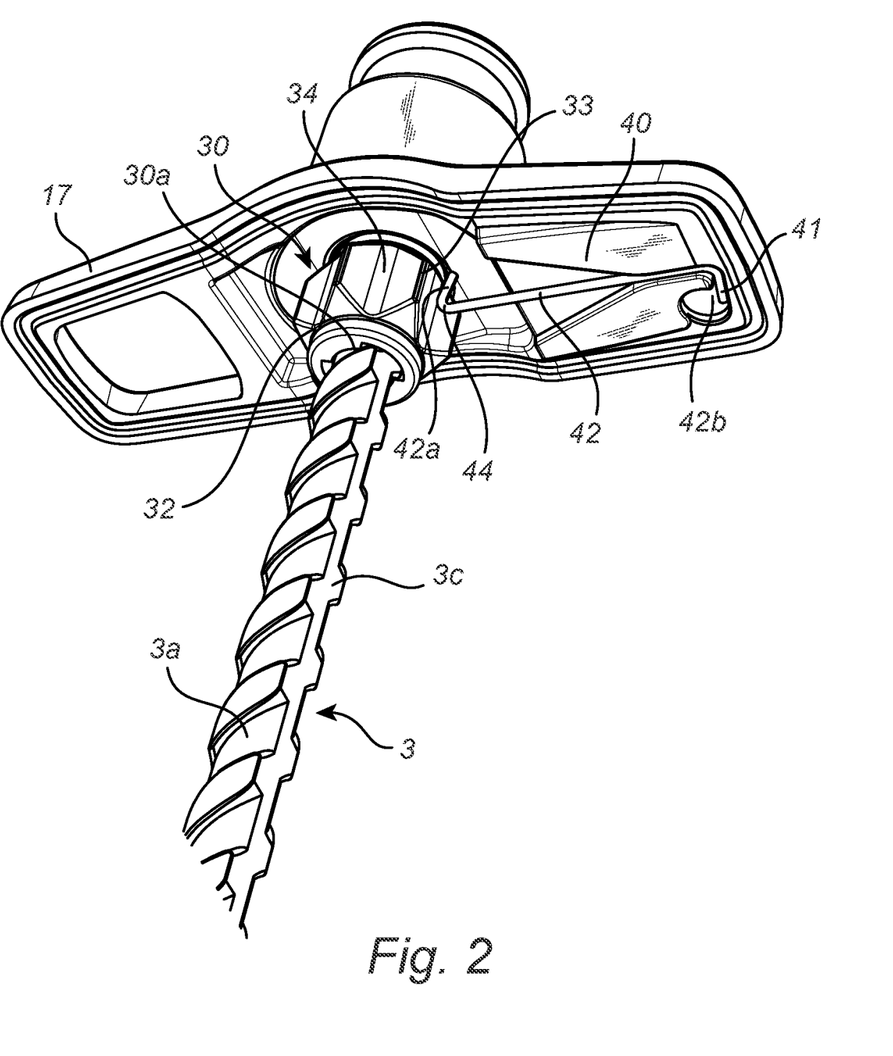
FIG. 2 is a detailed perspective view of some of the comprised components of a syringe according to an embodiment of the invention.

The syringe further comprises a first engagement member 30 arranged at the plunger rod 3, shown in more detail in FIG. 2. The first engagement member 30 has a substantially circular, or annular shape, i.e. may be described as having a wheel shape. Further, the first engagement member comprises a grooved surface 32 comprising a plurality of alternating ridges/ribs 33 and grooves 34 provided in an alternating manner along the surface 32. The grooved surface 32, and consequently the plurality of grooves and ridges, is/are provided along the circumference of the first engagement member 30.

The ridges (and grooves) typically comprise a symmetrical shape, although many shapes are conceivable, and may for example be provided by providing the first engagement member with a suitable number of grooves defined by flanges, or protrusions/ribs. The shape of the protrusions may vary depending on the field of use of the syringe. In the illustrated embodiment, the ridges (and grooves) extend in a direction substantially parallel to a longitudinal direction of the plunger rod.

In the illustrated embodiment, the ribs 33 of the grooved surface 32 are relatively large and the ribs 33 are further arranged at a comparatively large distance. The distance between the centre points of adjacent ridges 33 in the embodiment illustrated in FIG. 2 is typically between 1 and 3 mm.

The first engagement member 30 and the plunger rod 3 are adapted to engage such that a longitudinal movement of the plunger rod 3 yields at least a rotational movement of the first engagement member 30. In the illustrated embodiment, the engagement is achieved by means of a thread fitting between the plunger rod 3 and the first engagement member 30. The plunger rod 3 comprises helical groove 3a, and the first engagement member 30 comprises a corresponding protruding helical structure 30a, i.e. a thread fitting, which consequently is arranged at an inner surface of the first engagement member 30. Furthermore, the finger grip 17 comprises a through hole 49, through which the plunger rod extends. A guiding portion 50 is arranged at the hole 49. The guiding portion 50 is adapted to restrain a rotation of the plunger rod 3 such that the plunger rod 3 moves in a longitudinal direction while yielding a rotational movement of the first engagement member 30. In order to engage the guiding portion 50, the plunger rod 3 comprise a first substantially flat surface 3c, and an opposite second substantially flat surface (not shown) adapted to engage first and second corresponding flat surfaces 50a, 50b of the guiding portion 50, such that a rotation is constrained.

A second engagement member 40 is comprised by the embodiment shown in FIGS. 1 and 2, exemplary arranged at the finger grip 17. The second engagement member 40 is adapted to engage with the grooved surface 32 of the first engagement member in order to provide feedback to the user as the plunger rod 3, on which the first engagement member 30 is arranged, is moved with respect to the barrel 1. The second engagement member 40 is in the illustrated embodiment arranged at the finger grip 17 at an upper end 1b of the barrel 1. The second engagement member 40 comprises a movable, flexible structure 42, which may be referred to as a "click spring". The click spring 42 is elongated and made from a flexible, or resilient, material such as for example steel wire and comprises a plurality of bent portions. The second engagement member further comprises a spring fixation 41 adapted to receive a second end 42b of the click spring and to fix the second end 42b of the click spring 42 to the finger grip 17. A first, opposite, end 42a of the click spring 42, which may be referred to as an engaging member and/or a protruding portion, is adapted to engage the grooved surface of the first engagement member 30.

The click spring is adapted to move in a plane substantially perpendicular to a longitudinal direction of the plunger rod 3 as the plunger rod 3 moves relative to the barrel 1. The plane may further be described as a plane through the first engagement member, the first engagement member further also moves, i.e. rotates, in the plane. Further, the click spring 42 comprises an end portion 44, arranged at the first end of the spring adapted to engage the grooved surface 32, or to improve the engagement.

The wheel diameter and the pitch may be designed to allow the click spring to snap back to its initial position at a point corresponding to a desired dose size. Further, the pitch may be also be chosen based on other important, interacting, parameters of the syringe such as size of the first engagement member, in the illustrated case the diameter of the wheel, the number and shape of the grooves and ridges of the grooved surface as well as the design of the second engagement member, in the illustrated case most particularly the length of the click spring.

In the embodiment shown in FIGS. 1 and 2, the feedback provided by the click spring 42 of the second engagement member 40 interacting or engaging with the grooved surface 32 of the first engagement member 30 is an audible feedback, i.e. a sound. Each click corresponds to the click spring 42 of the second engagement member 40 travelling over one groove (or ridge) of the first engagement member. This functionality will be described in conjunction with the functionality of the engagement between the first engagement member 30 and the plunger rod 3 in the following.

The first engagement member 30 is arranged on the plunger rod 3 and consequently moves as the plunger rod 3 moves relative the barrel 1, the click spring 42 of the second engagement member 40 engages the ribs of the grooved surface 32 of the first engagement member 30 as the plunger rod 3 moves with respect to the barrel 1. In what may be described as a first stage of the engagement, the click spring 42, engages a first groove. This first stage may be described as an initial position wherein the click spring 42 is at rest, i.e. in a non-tensioned or relaxed state. As the plunger rod 3 moves longitudinally with respect to the barrel 1 and the first engagement member 30 consequently rotates, the click spring 42 deflects, i.e. moves outwards in a substantially radial direction of the click wheel when sliding up the next ridge of the grooved surface 32. This corresponds to the click spring sliding into a tensioned, or biased, stage of the click spring. Subsequently, the click spring 42 is to engage a second adjacent groove of the first engagement member, i.e. move into a stage of engagement corresponding again to the i.e. initial position of the click spring 42. After leaving the tip of the ridge, the second engagement member accelerates freely until stopped dead by the first engagement member when engaging the next groove, this stop, i.e. engagement, produces an audible sound, i.e. a "click-sound".

Accordingly, the engagement between the first and the second engagement member 30, 40 may be described at least in part as an engagement in a sense adapted to stop a free movement and an acceleration of the second engagement member 40, wherein the act of stopping the free movement/acceleration is such that an audible sound is produced. Accordingly, when the click spring 42 has climbed over one ridge, it accelerates back to the initial position and is stopped hard by the next rib, whereby a click sound is produced. The sound may be described as generated by the click spring acceleration and/or the hard stop at the next rib.

The relatively large ribs of the first engagement member 30, or click wheel 30, of the second embodiment gives an advantageous interaction with the click spring 42, since the large distance allows for the previously engaged rib (or ridge) to move away from the click spring 42 when the click wheel 30 is rotated. Accordingly, a free acceleration of the click spring back to the initial, unbiased, position may for example be allowed.

Further, the illustrated first engagement member 30, due to the large ribs, provides a relatively large "tensioned distance", i.e. the click spring 42 may be tensioned to a relatively high degree when in maximum deflection (i.e. at the top of a ridge). Due to the gear box mechanism provided by the thread, this large tension distance is possible without the need for the plunger rod to travel more than a dose size.

This gives that the click spring 42 may be released from the rib at a point corresponding to one dose size even though there is a large interaction distance that allows for more generous component tolerances in the mechanism.

With regards to the problems related to the size of a dose delivered following a change of direction of the plunger rod such as the first dose delivered after a substance has been drawn into the syringe, as described above the wheel diameter and the rib pitch of the disclosed syringe may be designed to allow the click spring to snap back to its initial position at a point corresponding to a desired dose size which implies a minimal difference in dose size.

While the invention has been illustrated and described in detail in the drawings and foregoing description, such illustration and description are to be considered illustrative or exemplary and not restrictive; the invention is not limited to the disclosed embodiments. The skilled person understands that many modifications, variations and alterations are conceivable within the scope as defined in the appended claims.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the claims.

The injection of botulinum toxin has been mentioned as a possible area of use for the device according to the invention. Naturally, it is possible to use the device according to the present invention with other liquid compositions, and gel compositions, such as hydrogels. The device is also useful for injecting cross linked or non-cross linked hyaluronic acid gels and other types of dermal fillers than hyaluronic acid, e.g. collagen, calcium hydroxyl apatite, poly-L-lactic acid (PLLA), other polysaccharides and polymethylmethacrylate (PMMA). Furthermore, the device is useful for injecting liquid compositions comprising active substances and/or bioactive agents, such as local anaesthetics, cicatrizants, antioxidants, insulin or growth hormones. One preferred liquid composition of this type is a gel composition with a hyaluronic acid gel carrier and an active substance and/or a bioactive agent, e.g. a local aesthetic or a cicatrizant, such as dextranomer beads.

The invention claimed is:

1. A syringe, comprising:
    a barrel,
    a plunger moveably arranged within said barrel and a plunger rod to drive said plunger,
    a finger grip at an upper end of said barrel,
    a first engagement member having a substantially circular shape arranged at the plunger rod such that longitudinal movement of the plunger rod yields rotational movement of said first engagement member, said first engagement member comprising a grooved surface; and
    a second engagement member comprising a movable flexible structure arranged at the finger grip at the barrel, the movable flexible structure being arranged to engage with said grooved surface of the first engagement member to give feedback comprising at least one of audible or tactile feedback to a user as the plunger rod is moved relative to the barrel for driving said plunger, wherein the movable flexible structure of the second engagement member comprises a first end and a second end, the first end being adapted to engage with the grooved surface of the first engagement member and the second end being fixed to the finger grip;
    wherein, for a given distance D travelled by the plunger rod relative to the barrel, a point of the grooved surface of the first engagement member moves a distance d, wherein d>D, and
    wherein the syringe is configured to deliver the same feedback regardless of a direction of movement of the plunger rod.

2. The syringe according to claim 1, wherein the first engagement member and the second member move substantially in a common plane A.

3. The syringe according to claim 2, wherein said plane A is a plane normal to the direction of movement of said plunger rod.

4. The syringe according to claim 1, wherein the plunger rod and the first engagement member are arranged such that a gear mechanism is provided by the engagement between said plunger rod and said first engagement member.

5. The syringe according to claim 1, wherein longitudinal movement of the plunger rod yields rotational movement of the first engagement member.

6. The syringe according to claim 1, further comprising a guiding element adapted to restrain rotational movement of said plunger rod.

7. The syringe according to claim 1, wherein said plunger rod comprises at least one of a helical groove or a helical protrusion.

8. The syringe according to claim 7, wherein said first engagement member comprises a fitting to engage said at least one of a helical groove or a helical protrusion.

9. The syringe according to claim 1, wherein at least a portion of said second engagement member is movable between a first stage, wherein said at least one portion of said second engagement member engages with a groove and a second stage, wherein said at least one portion of said second engagement member engages a protrusion.

10. The syringe according to claim 9, wherein said least one portion of said second engagement member is movable between said first stage and said second stage by a deflection.

11. The syringe according to claim 9, wherein at least a portion of the second engagement member is tensioned at least in said second stage.

12. The syringe according to claim 9, wherein said at least one portion of the second engagement member is untensioned in said first stage.

13. The syringe according to claim 1, wherein said second engagement member comprises an engaging member adapted to engage the grooved surface of the first engagement member.

14. The syringe according to claim 1, wherein:
the movable flexible structure comprises an elongated body disposed between a first bent portion including the first end and a second bent portion including the second end; and
each of the first end and the second end extends in a direction substantially perpendicular to the elongated body.

* * * * *